(12) United States Patent
Siegel et al.

(10) Patent No.: US 6,660,844 B1
(45) Date of Patent: Dec. 9, 2003

(54) OPTICAL SENSORS OF CELL SIGNALING

(75) Inventors: Micah S. Siegel, Berkeley, CA (US); Ehud Y. Isacoff, Berkeley, CA (US)

(73) Assignees: California Institute of Technology, Pasadena, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 08/957,484

(22) Filed: Oct. 24, 1997

Related U.S. Application Data (60) Provisional application No. 60/039,792, filed on Mar. 4, 1997, and provisional application No. 60/035,770, filed on Jan. 7, 1997.

(51) Int. Cl.[7] .................. C07K 14/00; A61K 38/02; A61K 38/17; C07H 21/04
(52) U.S. Cl. .................. 530/402; 530/300; 530/350; 435/6; 435/69.1; 435/69.7; 536/23.1
(58) Field of Search ............................. 530/350, 300, 530/402; 435/6, 69.1, 69.7; 536/23.1

(56) References Cited

U.S. PATENT DOCUMENTS 5,491,084 A  2/1996  Chalfie et al. ............... 435/189

OTHER PUBLICATIONS

Molloy, M. J et al, The Jellyfish green fluorescent protein:a new tool for studying ion channel expression and function, Neuron, vol. 14, No. 2, pp. 211–215, 1195.*

Kain, S. R. et al., green fluorescent proteins as a receptor of gene expression and protein localization. BioTechniques, vol. 19, No. 4, pp. 650–655, 1995.*

Mannuzzu, L. M. et al., Direct measurement of conformational rearrangement underlying potassium channel gatinf. Science, vol. 271, pp. 213–216, 1996.*

Venerando et al., "Mitochondrial alterations induced by aspirin in rat hepatocytes expressing mitochondrially targeted green fluorescent protein (mtGFP)", *FEBS Letter*, 382 (1996) 256–260.

Dopf et al., "Deletion mapping of the *Aequorea victoria* green fluorescent protein," *Gene*, 173 (1996) 39–44.

Htun et al., "Visualization of glucocorticoid receptor translocation and intranuclear organization in living cells with a green fluorescent protein chmera," *Proc. Natl. Acad. Sci. USA*, vol. 3, pp. 4845–4850, May 1996.

Carey et al., "Evidence Using a Green Fluorescent Protein–Glucocorticoid Receptor Chimera that the RAN/TC4 GTPase Mediates an Essential Function Independent of Nuclear Protein Import," *The Journal of Cell Biology*, vol. 33, No. 5, Jun. 1996, pp. 985–996.

Girotti et al., "TGN38–green fluorescent protein hybrid proteins expressed in stably transfected eukaryotic cells provide a tool for the real–time, in vivo study of membrane traffic pathways and suggest a possible role for ratTGN38", *Journal of Cell Science*, 109, 2915–2926 (1996).

Cubitt et al., "Understanding, improving and using green fluorescent proteins," *TIBS*, Nov. 1995, vol. 20, pp. 448–455.

\* cited by examiner

*Primary Examiner*—Gary Kunz
*Assistant Examiner*—Nirmal S. Basi
(74) *Attorney, Agent, or Firm*—Gray Cary Ware & Freidenrich, LLP; Lisa A. Haile; June M. Learn

(57) ABSTRACT

A chimeric protein sensor including an optically active polypeptide linked to a responsive polypeptide, or responsive fragment thereof, which undergoes a change in response to a cell signaling event, wherein an optical property of the sensor is altered in response to the change in the responsive polypeptide, or responsive fragment thereof is provided, as well as nucleic acid sequences encoding the chimeric protein sensor. The chimeric protein sensor includes an optically active polypeptide or fragment thereof, such as green fluorescent protein (GFP), for measuring cellular events in vivo.

5 Claims, 5 Drawing Sheets

SEQUENCE LISTING

```
<160> NUMBER OF SEQ ID NOS: 8

<210> SEQ ID NO 1
<211> LENGTH: 26
<212> TYPE: DNA
<213> ORGANISM: Artificial sequence
<220> FEATURE:
<223> OTHER INFORMATION: Oligonucleotide for PCR

<400> SEQUENCE: 1
ccactagtaa aggagaagaa cttttc                                        26

<210> SEQ ID NO 2
<211> LENGTH: 32
<212> TYPE: DNA
<213> ORGANISM: Artificial sequence
<220> FEATURE:
<223> OTHER INFORMATION: Oligonucleotide for PCR

<400> SEQUENCE: 2
ggactagtgc catgtgtaat cccagcagct gt                                 32

<210> SEQ ID NO 3
<211> LENGTH: 26
<212> TYPE: PRT
<213> ORGANISM: Homo sapiens

<400> SEQUENCE: 3

Met Leu Arg Thr Ser Ser Leu Phe Thr Arg Arg Val Gln Pro Ser Leu
1               5                   10                  15

Phe Arg Asn Ile Leu Arg Leu Gln Ser Thr
            20                  25

<210> SEQ ID NO 4
<211> LENGTH: 5
<212> TYPE: PRT
<213> ORGANISM: Homo sapiens

<400> SEQUENCE: 4

Lys Lys Lys Arg Lys
1               5

<210> SEQ ID NO 5
<211> LENGTH: 4
<212> TYPE: PRT
<213> ORGANISM: Homo sapiens

<400> SEQUENCE: 5

Lys Asp Glu Leu
1

<210> SEQ ID NO 6
<211> LENGTH: 4
<212> TYPE: PRT
<213> ORGANISM: Homo sapiens
<220> FEATURE:
```

```
<221> NAME/KEY: MISC_FEATURE
<222> LOCATION: (4)..(4)
<223> OTHER INFORMATION: Xaa is any Amino Acid

<400> SEQUENCE: 6

Cys Ala Ala Xaa
1

<210> SEQ ID NO 7
<211> LENGTH: 4
<212> TYPE: PRT
<213> ORGANISM: Homo sapiens
<220> FEATURE:
<221> NAME/KEY: MISC_FEATURE
<222> LOCATION: (3)..(4)
<223> OTHER INFORMATION: Xaa is any Amino Acid

<400> SEQUENCE: 7

Cys Cys Xaa Xaa
1

<210> SEQ ID NO 8
<211> LENGTH: 238
<212> TYPE: PRT
<213> ORGANISM: Aequorea victoria

<400> SEQUENCE: 8

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

OPTICAL SENSORS OF CELL SIGNALING

CROSS REFERENCE TO RELATED APPLICATIONS

This application claims benefit under 35 U.S.C. §119(e) of provisional application Ser. No. 60/035,770, filed Jan. 7, 1997, and No. 60/039,792, filed Mar. 4, 1997, each of which is incorporated herein by reference in its entirety.

BACKGROUND OF THE INVENTION

This invention relates generally to the field of cellular signaling, and more specifically to methods for measuring changes that occur during a cell signaling event using optical sensors having fluorescent properties.

FIELD OF THE INVENTION

Fluorescent indicator dyes revolutionized the understanding of cellular physiology by providing a means for continuous measurements in single cells and cell populations. Presently, these dyes are synthesized chemically and introduced as hydrolyzable esters or by microinjection (Cohen, L., and Lesher, S. (1986) Soc. Genl. Physiologists, 40:71–99; Gross, D., and Loew, L. M. (1989) Methods in Cell Biology, 30:193–218; Tsien, R. Y. (1989) Ann. Rev. Neuroscience, 12:227–253). Delivering indicator dyes to specific cell populations has proven to be a difficult problem. In the absence of such cell-specific localization, optical measurement in a tissue cannot distinguish the particular cell population that initiates a signal.

Fluorescent proteins have been used as markers of gene expression, tracers of cell lineage, and fusion tags to monitor protein location within cells (e.g., Chalfie, M., et al., Science 263:802–5). Green fluorescent protein (GFP), a small protein, consisting of only 238 amino acids, has been cloned from *Aequorea victoria* (Prasher, D. C., et al. (1992) Gene, 111:229–233). The chromophore of GFP is generated autocatalytically (Heim, R., et al. (1994) Proc. Nat'l. Acad. Sci. USA, 91: 12501–12504), and the protein is stable and functional in many cell types. The crystal structure of GFP has been solved by X-ray diffraction (Ormo, M., et al. (1996) Science, 273:1392–1395; Yang, F., et al. (1996) Nat. Biotechnol., 14:1246–1251). Mutant versions of the green fluorescent protein have been identified that exhibit altered fluorescence characteristics, including different excitation and emission maxima. Fluorescent molecules are attractive as sensors because of the ease of quantification and the highly sensitive nature of the assays. Fluorescent proteins can be produced in vivo by biological systems, and can be used to trace intracellular events. GFP has been shown to fluoresce when expressed from the cDNA, indicating that the protein can undergo the cyclization and oxidation necessary for fluorescence in vivo.

Despite the tremendous advances in the field of genetic engineering and expression of a DNA of interest in a desired cell, few tools exist in the art for the direct, selective measurement of a specific physiological response in a cell. For example, although cell growth can be stimulated during in vitro culture by inclusion of growth factors in the culture medium, there are few adequate means available to directly measure changes in cellular events in response to growth factor administration.

SUMMARY OF THE INVENTION

This invention provides optical sensors for measuring cell signaling or cellular events in vitro or in vivo. The sensors of the invention are chimeric proteins including an optically active polypeptide or fragment thereof, operatively linked to a responsive polypeptide, or responsive fragment thereof. The chimeric protein typically exists in a particular state prior to a cellular event, which state measurably changes during or following the event. Depending on the conformational shape or the state assumed by the expressed protein, a property of the optically active polypeptide changes (e.g., a fluorescence characteristic), thereby making it possible to differentiate between an event before and after it has occurred, and thus an activity of the cell, via the optical output.

In one embodiment, the invention features nucleic acid sequences which encode a chimeric protein including an optically active polypeptide linked to a responsive polypeptide, or responsive fragment thereof, which undergoes a change in response to a cell signaling event and wherein an optical property of the sensor is altered in response to the change. Preferably, the optically active polypeptide or fragment thereof is a fluorescent protein such as GFP.

In another embodiment, the invention features a method for determining the presence of an activity in a sample including contacting the sample with a chimeric protein of the invention; exciting the chimeric protein; and measuring the amount of an optical property in the presence and absence of activity, such that a change in the optical property is indicative of activity. The invention also features a method for determining if a cell exhibits an activity, which includes transfecting a cell with a nucleic acid encoding a chimeric protein of the invention; exciting the chimeric protein; and measuring the amount of an optical property in the presence of the activity and in the absence of the activity, such that a change in the optical property is indicative of activity.

The invention also includes a method for determining whether a compound alters a cell signaling event, including contacting a sample containing a known amount of a cell signaling activity with a test compound and a chimeric protein of the invention; exciting the chimeric protein; measuring the amount of cell signaling activity in the sample as a function of the quantity of change or rate of change of an optical property that differs before and after the cell signaling event; and comparing the amount of activity in the sample with a standard activity for the same amount of the cell signaling event, whereby a difference between the amount of activity in the sample and the standard activity indicates that the compound alters a cell signaling event.

In yet another embodiment, the invention provides a kit for determining the presence of an activity in a sample, including either a chimeric protein of the invention, or a nucleic acid sequence encoding a chimeric protein of the invention. The kit including a nucleic acid encoding a chimeric sensor protein of the invention may provide a host cell stably transfected with the nucleic acid sequence, wherein the cell is now an optical indicator. Thus, the invention also provides a recombinant cell line containing the chimeric protein of the invention. In a specific example provided herein, the responsive polypeptide is a voltage-gated ion channel and the optically active polypeptide is GFP, more specifically, a deletion mutant of GFP. Other modified GFPs are useful in the invention.

Another embodiment of the invention provides a non-human transgenic animal, such as a mouse, which has incorporated into its genome a recombinant nucleic acid sequence encoding a chimeric protein of the invention.

BRIEF DESCRIPTION OF THE DRAWINGS

FIGS. 4A, 4B, 4C, 4D, 4E, 4F, and 4G, respectively, are graphs showing fluorescence changes in response to voltage steps between −80V and +40V, in 20V increments. Scale of x and y axis is shown by the bar on each axis.

DESCRIPTION OF THE PREFERRED EMBODIMENTS

Chimeric Proteins

The sensors of the invention are chimeric proteins having an optically active polypeptide in operative linkage with a responsive polypeptide, or responsive fragment thereof. The chimeric protein or responsive polypeptide normally exists in one state e.g., conformational shape or charge, prior to a cellular event or cell signaling event, and undergoes a change during or after a cell signaling event. Depending on the state assumed by the chimeric polypeptide, an optical property of the sensor will change, thereby making it possible to differentiate between states of the polypeptide, and thus the activity of the cell, via the optical output. An advantage of the invention is that the sensitivity and range of operation of sensors of the invention are determined by the responsive polypeptide or the chimeric polypeptide, thus the sensors are able to detect biologically relevant signals. Calibration of the sensors also allows translation of the optical parameter (e.g., units of fluorescence) into units of activity.

"A cell signaling event", "cellular event" or "cell signaling" as used herein refers to the generation of a biochemical or physiological response as a result of an event occurring during cellular metabolism, regulation, growth, differentiation, stimulation, division, or death. In general, cell signaling events result in a change of a molecular characteristic of the cell as compared to the characteristic prior to the event.

A "chimeric" polypeptide as used herein refers to a polypeptide containing all or a fragment of amino acid sequence derived from one protein connected, linked or fused with all or a fragment of amino acid sequence derived from at least one other protein. The amino acid sequences can be linked contiguously, or end to end, as in a standard fusion protein, or can be rearranged within each other, so long as the biological or functional activities of each protein or fragment thereof are retained. For example, the chimeric protein of the invention contains at least one polypeptide of fragment thereof which is the "responsive" polypeptide and one which is the "optically active" polypeptide. In an illustrative example provided herein, a Shaker channel polypeptide is fused in operative linkage with a truncated GFP (deletion mutation at amino acid residues 233–238). Given the teachings herein and the knowledge of those of skill in the art, it would not require undue experimentation to construct other chimeric or fusion proteins useful as optical sensors as described in the present invention.

"Operative linkage" between the responsive polypeptide and the optically active polypeptide refers to refers to a juxtaposition wherein the components so described are in a relationship permitting them to function in their intended manner. A responsive polypeptide operatively linked to an optically active polypeptide is connected such that the optically active polypeptide is responsive to a "change" in the responsive polypeptide in response to a cellular or cell signaling event.

The "responsive polypeptide" is any polypeptide that may undergo a change in a state of the polypeptide during a cell signaling event. The responsive polypeptide may be "responsive" prior to or following construction of a chimeric polypeptide of the invention. In other words, the operative linkage with an optically active polypeptide may provide responsiveness to the polypeptide. Such changes or states include conformational changes, change in charge, and change in phosphorylation or methylation status, dimerization status, protein/protein or protein/nucleic acid interaction, for example.

As used in connection with the present invention, the term "polypeptide" refers to a polymer in which the monomers are amino acid residues which are joined together through amide bonds. When the amino acids are alpha-amino acids, either the L-optical isomer or the D-optical isomer can be used, the L-isomers being preferred. The terms "polypeptide" as used herein is intended to encompass any amino acid sequence and include modified sequences such as glycoproteins. The term "polypeptide" is specifically intended to cover naturally occurring proteins, as well as those which are recombinantly or synthetically synthesized, which occur in at least two different conformations wherein both conformations have the same or substantially the same amino acid sequence but have different three dimensional structures.

"Conformation" is the three-dimensional arrangement of side groups in a molecule; a change in conformation occurs when the three-dimensional structure of a molecule changes. Examples of conformational changes include a shift from $\alpha$-helix to a $\beta$-sheet or a shift from $\beta$-sheet to a $\alpha$-helix.

"Fragments" as used herein are a portion of a naturally occurring protein which can exist in at least two different states or conformations. Fragments can have the same or substantially the same amino acid sequence as the naturally occurring protein. "Substantially the same" means that an amino acid sequence is largely, but not entirely, the same, but retains a functional activity of the sequence to which it is related. In general two amino acid sequences are substantially the same" or "substantially homologous" if they are at least 85% identical. Fragments which have different three dimensional structures as the naturally occurring protein are also included. The term "responsive" as used herein is intended to encompass any change in a polypeptide that occurs following a particular cell signaling event, which is directly or indirectly caused by that cell signaling event (e.g., conformational change in a voltage-gated ion channel (e.g., Shaker) in detection of membrane voltage across the cell; phosphorylation of a hormone receptor resulting in a conformational change in the receptor upon hormone stimulation).

Classes of responsive polypeptides the invention include, but are not limited to, channel proteins, receptors, enzymes, and G-proteins. Channel polypeptides useful with the invention include, but are not limited to voltage-gated ion channels including the potassium, sodium, chloride, G-protein-responsive, and calcium channels. A "channel polypeptide" is a polypeptide embedded in the cell membrane which is part of a structure that determines what particle sizes and or charges are allowed to diffuse into the cell. Channel polypeptides include the "voltage-gated ion channels", which are proteins imbedded in a cell membrane that serve as a crossing point for the regulated transfer of a specific ion or group of ions across the membrane. Several ion channel polypeptides of use with the invention are listed in Table I.

TABLE I

Ion Channels

| Gene Product | Genbank Accession No. |
| --- | --- |
| Human voltage-gated chloride ion channel CLCN5 | X91906 |
| Human delayed rectifier potassium channel (Isk) gene | L33815 |
| Human potassium channel protein (HPCN3) gene | M55515 |
| Human potassium channel (HPCN2) (mRNA) | M55514 |
| Human potassium channel (HPCN1) (mRNA) | M55513 |
| Human gamma subunit of epithelial amiloride-sensitive sodium channel (mRNA) | X87160 |
| Human beta subunit of epithelial amiloride-sensitive sodium channel | X87159 |

Channels also include those activated by intracellular signals such as those where the signal is by binding of ligand such as calcium, cyclic nucleotides, G-proteins, phosphoinositols, arachidonic acid, for example, and those where the signal is by a covalent modification such as phosphorylation, enzymatic cleavage, oxidation/reduction, and acetylation, for example. Channel proteins also include those activated by extracellular ligands (e.g., ionotropic receptors). These can be activated by acetylcholine, biogenic amines, amino acids, and ATP, for example.

A "receptor polypeptide" is a polypeptide found on a cell, often on a membrane, that can combine with a specific type of molecule, e.g., a ligand, which alters a function of the cell. Receptor polypeptides of use with the invention include, but are not limited to, the growth factor receptors, hormone receptors, cytokine receptors, neurotransmitter receptors, ligand-gated channels, and steroid receptors. Specifically polypeptides encoding insulin-like growth factor, insulin, somatostatin, glucagon, interleukins, e.g., IL-2, transforming growth factors (TGF-α, TGF-β), platelet-derived growth factor (PDGF), epidermal growth factor (EGF), nerve growth factor (NGF), fibroblast growth factor (FGF), interferon-γ (IFN-γ), and GM-CSF receptors are of use with the invention. Receptors are "metabotropic", such as those where binding of ligand is transmitted to a G-protein (e.g., for 7-transmembrane receptors) or kinase domains (for single transmembrane receptors). These can be activated by acetylcholine, biogenic amines, amino acids, ATP, and many peptides, such as opioids, hypothalamic-releasing hormones, neurohypophyseal hormones, pituitary hormones, tachykinins, secretins, insulins, somatostatins, and gastrointestinal peptides. Several receptor polypeptides of use with the invention are listed in Table II.

TABLE II

Receptors

| Gene Product | Genbank Accession No. |
| --- | --- |
| Human insulin receptor gene | M29929 |
| Human somatostatin receptor gene | L14856 |
| Human IL-2 receptor gene | X01057, X01058, XD1402 |
| Human TGF receptor (mRNA) | M8509 |
| Human PDGF receptor (mRNA) | M22734 |
| Human EGF receptor gene | X06370 |
| Human NGF receptor (mRNA) | M14764 |
| Human FGF receptor (mRNA) | M34641 |
| Human GM-CSF receptor (mRNA) | M73832 |
| Human IFN-γ receptro (mRNA) | X62468 |

An "enzyme" is a polypeptide that acts as a catalyst, which speeds the rate at which biochemical reactions proceed do not alter the direction or nature of the reaction. Enzyme polypeptides useful in the invention include, but are not limited to, protein kinases, catalyses, amidase, phosphatases, guanylyl and adenylyl cyclases, and lipoxygenases. Polypeptides encoding the serine/threonine protein kinases are of use with the invention. Several genes encoding human enzymes of use with the invention are listed in Table III.

TABLE III

Enzymes

| Gene Product | Genbank Accession No. |
| --- | --- |
| Human cAMP dependent protein kinase AKAD 79 (mRNA) | M90359 |
| Human protein kinase C beta gene | D10022 |
| Human lipid-activate protein kinase PRK-1 (mRNA) | U33053 |
| Human guanine nucleotide binding protein alpha subunit gene | M21142, J03647, M21139 |
| Human serine/theronine kinase (mRNA) | M83780 |

The change in conformation or state that occurs in the responsive peptide during cell signaling or cellular events results in a change in an optical characteristic of the sensor. The change can be the result of an alteration in the environment, structure, or oligomerization status of the sensor. The molecular component responsible for a conformational change is known for many enzymes (e.g., Blostien, R., et al. (1997) J. Biol. Chem., 272:24987–93; Shoelstein, Se. E., et al., (1993) EMBO J., 12:795–802), receptors (e.g. Moyle, W. R., et al., (1995) J. Biol. Chem., 270:20020–20031; Baron, V., et al., (1992), J. Biol. Chem. 267:23290–23294), and channels (e.g., Bouzat. A., et al., (1994) Neuron, 13: 1395–1402; Dulhanty, A. M., (1994) Biochemistry, 33:4072–79). The optical properties of the sensor which can be altered in response to the conformational change in the responsive polypeptide include, but are not limited to, changes in the excitation or emission spectrum, quantum yield, extinction coefficient, excited lifetime and degree of self-quenching for example. The cause of the changes in these parameters may include but are not limited to changes in the environment, changes in the rotational or vibrational freedom of the sensor, changes in the angle of the sensor with respect to the exciting light or the optical detector apparatus, or changes in distance or dipole orientation between sensors on associated responsive polypeptides.

In the chimeric proteins of the invention, the responsive polypeptide is operably linked to an optically active polypeptide. A protein-based "optically active polypeptide" is a polypeptide which contains a means for emitting light. Fluorescence is one optical property of an optically active polypeptide which can be used as the means of detecting a conformational change of the responsive polypeptide of the chimeric proteins of the invention. As used herein, the term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between the active and inactive states suffices for the utility of the fluorescent protein substrates of the invention in assays for activity. A measurable difference can be determined by determining the amount of any quantitative fluorescent property, e.g., the amount of fluorescence at a particular wavelength, or the integral of fluorescence over the emission spectrum. Optimally, the protein substrates are selected to have fluorescent properties that are easily distinguishable in the un-activated and activated conformational states.

One means of measuring fluorescence in a sample uses a fluorimeter. In general, excitation radiation, from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation. Other means of measuring fluorescence can also be used with the invention.

Methods of performing assays on fluorescent materials are well known in the art and are described in, e.g., Lakowicz, J. R., *Principles of Fluorescence Spectroscopy*, New York:Plenum Press (1983); Herman, B., Resonance energy transfer microscopy, in: *Fluorescence Microscopy of Living Cells in Culture, Part B, Methods in Cell Biology*, vol. 30, ed. Taylor, D. L. & Wang, Y.-L., San Diego: Academic Press (1989), pp. 219–243; Turro, N. J., *Modern Molecular Photochemistry*, Menlo Park: Benjamin/Cummings Publishing Col, Inc. (1978), pp. 296–361.

Any fluorescent protein can be used in the invention, including proteins that fluoresce due to intramolecular rearrangements or the addition of cofactors that promote fluorescence. For example, green fluorescent proteins of cnidarians, which act as their energy-transfer acceptors in bioluminescence, are suitable fluorescent proteins for use in the fluorescent indicators. A green fluorescent protein ("GFP") is a protein that emits green light, and a blue fluorescent protein ("BFP") is a protein that emits blue light. GFPs have been isolated from the Pacific Northwest jellyfish, *Aequorea victoria,* the sea pansy, *Renilla reniformis,* and *Phialidium gregarium.* See, Ward, W. W., et al., *Photochem. Photobiol.,* 35:803–808 (1982); and Levine, L. D., et al., *Comp. Biochem. Physiol.,* 72B:77–85 (1982).

A variety of Aequorea-related GFPs having useful excitation and emission spectra have been engineered by modifying the amino acid sequence of a naturally occurring GFP from *Aequorea victoria.* (See, Prasher, D. C., et al., *Gene,* 111:229–233 (1992); Heim, R., et al., *Proc. Natl. Acad. Sci., USA,* 91:12501–04 (1994); U.S. Pat. Nos. 5,491,084; 5,625,048). The cDNA of GFP can be concatenated with those encoding many other proteins; the resulting chimerics often are fluorescent and retain the biochemical features of the partner proteins. (See, Cubitt, A. B., et al., *Trends Biochem. Sci.* 20:448–455 (1995)). Mutagenesis studies have produced may GFP mutants, some having shifted wavelengths of excitation or emission. Such proteins are included in the invention sensor. A fluorescent protein is an "Aequorea-related fluorescent protein" if any contiguous sequence of 150 amino acids of the fluorescent protein has at least 85% sequence identity with an amino acid sequence, either contiguous or non-contiguous, from the wild type Aequorea green fluorescent protein. More preferably, a fluorescent protein is an Aequorea-related fluorescent protein if any contiguous sequence of 200 amino acids of the fluorescent protein has at least 95% sequence identity with an amino acid sequence, either contiguous or non-contiguous, from the wild type Aequorea green fluorescent protein. Similarly, the fluorescent protein can be related to Renilla or Phialidium wild-type fluorescent proteins using the same standards.

The fluorescent indicators can be produced as chimeric proteins by recombinant DNA technology. Recombinant production of fluorescent proteins involves expressing nucleic acids having sequences that encode the proteins. Nucleic acids encoding fluorescent proteins can be obtained by methods known in the art. For example, a nucleic acid encoding the protein can be isolated by polymerase chain reaction of cDNA from *A. victoria* using primers based on the DNA sequence of *A. victoria* green fluorescent protein. PCR methods are described in, for example, U.S. Pat. No. 4,683,195; Mullis, et al. *Cold Spring Harbor Symp. Quant. Biol.* 51:263 (1987), and Erlich, ed., *PCR Technology,* (Stockton Press, NY, 1989). Mutant versions of fluorescent proteins can be made by site-specific mutagenesis of other nucleic acids encoding fluorescent proteins, or by random mutagenesis caused by increasing the error rate of PCR of the original polynucleotide with 0.1 mM $MnCl_2$ and unbalanced nucleotide concentrations.

In a particular embodiment of the present invention, a C-terminal truncated GFP (GFPAΔ233–238; numbers refer to amino acid residues) is utilized in the chimeric protein (see Examples). This C-terminal deletion mutant was fused in-frame into the Shaker-ion channel into a region just after the sixth putative transmembrane helix (at the SpeI site). Thus, in another embodiment of the invention is provided a new GFP as an optically active polypeptide or optically active fragment of wild-type GFP. Other GFPs having C-terminal mutations are included in the invention.

In the chimeric proteins of the invention, the responsive polypeptide is operably linked to an optically active polypeptide, which changes conformation in response to a cell signaling event. Cell signaling events that occur in vivo can be of very short duration. The optically active polypeptides of the invention allow measurement of the optical parameter, such as fluorescence, which is altered in response to the cell signal, over the same time period that the event actually occurs. Alternatively, the response can be measured after the event occurs (over a longer time period) as the conformational change that occurs in an optically active polypeptide can be of a longer duration than the cell signaling event itself.

Nucleic Acid Constructs of the Invention

In another embodiment, the invention provides isolated nucleic acid sequences which encode an optically active polypeptide operatively linked to a responsive polypeptide, or fragment thereof, which normally exists in one state e.g., conformational shape or charge, prior to a cellular event or cell signaling event, and undergoes a change during or after a cell signaling event.

"Polynucleotide" or "nucleic acid sequence" refers to a polymeric form of nucleotides at least 10 bases in length. By "isolated nucleic acid sequence" is meant a polynucleotide that is not immediately contiguous with both of the coding sequence with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryotic or eukaryotic cell or organism, or which exists as a separate molecule (e.g. a cDNA) independent of other sequences. The nucleotides of the invention can be ribonucleotides, deoxyribonucleotides, or modified forms of either nucleotide. The term includes single and double stranded forms of DNA.

Nucleic acid sequences which encode an optically active polypeptide operatively linked to a responsive polypeptide, or fragment thereof, which normally has two or more states or conformational arrangements, and which undergoes a change during a cell signaling event can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and chimeric partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., 1987, Methods in Enzymology 153:516–544). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter; CMV promoter) may be used. Promoters produced by recombinant DNA or synthetic techniques may also be used to provide for transcription of the nucleic acid sequences of the invention.

In the present invention, the nucleic acid sequences encoding the chimeric protein of the invention may be inserted into a recombinant expression vector. The term "recombinant expression vector" refers to a plasmid, virus or other vehicle known in the art that has been manipulated by insertion or incorporation of the nucleic acid sequences encoding the chimeric peptides of the invention. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*,56:125, 1987), the pMSXND expression vector, or adeno or vaccinia viral vectors for expression in mammalian cells (Lee and Nathans, *J. Biol. Chem.*, 263:3521, 1988), baculovirus-derived vectors for expression in insect cells, cauliflower mosaic virus, CaMV; tobacco mosaic virus, TMV.

The nucleic acid sequences encoding an optically active polypeptide of the invention can also include a localization sequence to direct the indicator to particular cellular sites by fusion to appropriate organellar targeting signals or localized host proteins. A polynucleotide encoding a localization sequence, or signal sequence, can be ligated or fused at the 5' terminus of a polynucleotide encoding the fluorescence indicator such that the signal peptide is located at the amino terminal end of the resulting chimeric polynucleotide/polypeptide. In the case of eukaryotes, the signal peptide is believed to function to transport the chimeric polypeptide across the endoplasmic reticulum. The secretory protein is then transported through the Golgi apparatus, into secretory vesicles and into the extracellular space or, preferably, the external environment. Signal peptides which can be utilized according to the invention include pre-pro peptides which contain a proteolytic enzyme recognition site. Other signal peptides with similar properties to those described herein are known to those skilled in the art, or can be readily ascertained without undue experimentation.

The localization sequence can be a nuclear localization sequence, an endoplasmic reticulum localization sequence, a peroxisome localization sequence, a mitochondrial localization sequence, or a localized protein. Localization sequences can be targeting sequences which are described, for example, in "Protein Targeting", Chapter 35 of Stryer, L., *Biochemistry* (4th ed.), W. H. Freeman, 1995. The localization sequence can also be a localized protein. Some important localization sequences include those targeting the nucleus (KKKRK), SEQ ID NO:4 mitochondrion (amino terminal MLRTSSLFTRRVQPSLFRNILRLQST SEQ ID NO:3-), endoplasmic reticulum (KDEL SEQ ID NO:5 at C-terminus, assuming a signal sequence present at N-terminus), peroxisome (SKF at C-terminus), synapses (S/TDV or fusion to GAP 43, kinesin and tau) prenylation or insertion into plasma membrane (CaaX, SEQ ID NO:6, CC, CXC, or CCXX SEQ ID NO:7 at C-terminus), cytoplasmic side of plasma membrane (chimeric to SNAP-25), or the Golgi apparatus (chimeric to furin). The construction of expression vectors and the expression of genes in transfected cells involves the use of molecular cloning techniques also well known in the art. Sambrook et al., *Molecular Cloning— A Laboratory Manual,* Cold Spring Harbor Laboratory, Cold Spring Harbor, N.Y., (1989) and *Current Protocols in Molecular Biology,* F. M. Ausubel et al., eds., (Current Protocols, a joint venture between Greene Publishing Associates, Inc. and John Wiley & Sons, Inc., most recent Supplement). These methods include in vitro recombinant DNA techniques, synthetic techniques and in vivo recombination/genetic recombination. (See, for example, the techniques described in Maniatis, et al., *Molecular Cloning A Laboratory Manual,* Cold Spring Harbor Laboratory, N.Y., 1989).

Further, expression of the chimeric protein sensor of the invention can be targeted in a tissue specific manner, wherein the promoter is tissue specific. Examples of cells which can be targeted include but are not limited to a neural cell, an endocrine cell, a glial cell, a secretory cell, an immune cell, a muscle cell, an epithelial cell, a liver cell, and an exocrine cell. Promoters or expression control sequences can also target expression to a developmental stage or to a location within a cell, as discussed above. Such locations include the plasma membrane, the nuclear membrane, the Golgi apparatus, the endoplasmic reticulum, mitochondria, and lysosome. Specific regions of a cell that can be targeted include the apical surface, the basolateral surface, the dendrites, a presynaptic region, a postsynaptic region, and the axons.

Depending on the vector utilized, any of a number of suitable transcription and translation elements, including constitutive and inducible promoters, transcription enhancer elements, transcription terminators, etc. may be used in the expression vector (see, e.g., Bitter, et al., Methods in Enzymology 153:516–544, 1987). These elements are well known to one of skill in the art.

In bacterial systems a number of expression vectors may be advantageously selected depending upon the intended use. For example, when large quantities of a protein of the invention is desired, vectors which direct the expression of high levels of chimeric protein products that are readily purified may be desirable. Those which are engineered to contain a cleavage site to aid in protein recovery are preferred.

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., Expression and Secretion Vectors for Yeast, in Methods in Enzymology, Eds. Wu & Grossman, 31987, Acad. Press, N.Y., Vol. 153, pp.516–544, 1987; Glover, DNA Cloning, Vol. II, IRL Press, Wash., D.C., Ch. 3, 1986; and Bitter, Heterologous Gene Expression in Yeast, Methods in Enzymology, Eds. Berger & Kimmel, Acad. Press, N.Y., Vol. 152, pp. 673–684, 1987; and The Molecular Biology of the Yeast Saccharomyces, Eds. Strathern et al., Cold Spring Harbor Press, Vols. I and II, 1982. A constitutive yeast promoter such as ADH or LEU2 or an inducible promoter such as GAL may be used (Cloning in Yeast, Ch. 3, R. Rothstein In: DNA Cloning Vol.11, A Practical Approach, Ed. D M Glover, IRL Press, Wash., D.C., 1986). Alternatively, vectors may be used which promote integration of foreign DNA sequences into the yeast chromosome.

An alternative expression system which could be used to express the proteins of the invention is an insect system. In one such system, *Autographa californica* nuclear polyhedrosis virus (AcNPV) is used as a vector to express foreign genes. The virus grows in *Spodoptera frugiperda* cells. The sequence encoding a protein of the invention may be cloned into non-essential regions (for example, the polyhedrin gene) of the virus and placed under control of an AcNPV promoter (for example the polyhedrin promoter). Successful insertion of the sequences coding for a protein of the invention will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith, et al., *J. Viol.* 46:584, 1983; Smith, U.S. Pat. No. 4,215,051.

By "transformation" is meant a permanent genetic change induced in a cell following incorporation of new DNA (i.e. DNA exogenous to the cell). Where the cell is a mammalian cell, the permanent genetic change is generally achieved by introduction of the DNA into the genome of the cell.

By "transformed cell" is meant a cell into which (or into an ancestor of which has been introduced), by means of recombinant DNA techniques, a DNA molecule encoding a chimeric protein consisting of an optically active polypeptide operatively fused to a responsive polypeptide, or fragment thereof, which normally has two or more conformational shapes, and which undergoes a conformational change during a cell signaling or cellular event.

Transformation of a host cell with recombinant DNA may be carried out by conventional techniques as are well known to those skilled in the art. Where the host is prokaryotic, such as *E. coli,* competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the chimeric polypeptide of the invention, and a second foreign DNA molecule encoding a selectable phenotype, such as the herpes simplex thymidine kinase gene. Another method is to use a eukaryotic viral vector, such as simian virus 40 (SV40) adenovirus, vaccinia virus, or bovine papilloma virus, to transiently infect or transform eukaryotic cells and express the protein. (*Eukaryotic Viral Vectors,* Cold Spring Harbor Laboratory, Gluzman ed., 1982). Preferably, a eukaryotic host is utilized as the host cell as described herein. Methods of stable transfer, meaning that the foreign DNA is continuously maintained in the host, are known in the art.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, secretion of the gene product should be used as host cells for the expression of fluorescent indicator. Such host cell lines may include but are not limited to CHO, VERO, BHK, HeLa, COS, MDCK, Jurkat, HEK-293, and WI38.

Mammalian cell systems which utilize recombinant viruses or viral elements to direct expression may be engineered. For example, when using adenovirus expression vectors, the nucleic acid sequences encoding a chimeric protein of the invention may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the fluorescent indicator in infected hosts (e.g., see Logan & Shenk, *Proc. Natl. Acad. Sci. USA,* 81: 3655–3659, 1984). Alternatively, the vaccinia virus 7.5K promoter may be used. (e.g., see, Mackett, et al., *Proc. Natl. Acad. Sci. USA,*79: 7415–7419, 1982; Mackett, et al., *J. Virol.* 49: 857–864, 1984; Panicali, et al., *Proc. Natl. Acad. Sci. USA* 79: 4927–4931, 1982). Of particular interest are vectors based on bovine papilloma virus which have the ability to replicate as extrachromosomal elements (Sarver, et al., *Mol. Cell. Biol.* 1: 486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the fluorescent indicator gene in host cells (Cone & Mulligan, *Proc. Natl. Acad. Sci. USA,* 81:6349–6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the cDNA encoding a chimeric protein of the invention controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., *Cell,* 11: 223, 1977), hypoxanthine-guanine phosphoribosyltransferase (Szybalska & Szybalski, *Proc. Natl. Acad. Sci. USA,* 48:2026, 1962), and adenine phosphoribosyltransferase (Lowy, et al., *Cell,* 22: 817, 1980) genes can be employed in tk⁻, hgprt⁻ or aprt⁻ cells respectively. Also, antimetabolite resistance can be used as the basis of selection for dhfr, which confers resistance to methotrexate (Wigler, et al., *Proc. Natl. Acad. Sci. USA,* 77: 3567, 1980; O'Hare, et al., *Proc. Natl. Acad. Sci. USA,* 8: 1527, 1981); gpt, which confers resistance to mycophenolic acid (Mulligan & Berg, *Proc. Natl. Acad. Sci. USA,* 78: 2072, 1981; neo, which confers resistance to the aminoglycoside G-418 (Colberre-Garapin, et al., *J. Mol. Biol.,* 150:1, 1981); and hygro, which confers resistance to hygromycin (Santerre, et al., *Gene,* 30: 147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA,* 85:8047, 1988); and ODC (omithine decarboxylase) which confers resistance to the omithine decarboxylase inhibitor, 2-(difluoromethyl)-DL-omithine, DFMO (McConlogue L., In: *Current Communications in Molecular Biology,* Cold Spring Harbor Laboratory, ed., 1987).

A chimeric protein of the invention can be produced by expression of nucleic acid encoding the protein in prokaryotes. These include but are not limited to microorganisms such as bacteria transformed with recombinant bacteriophage DNA, plasmid DNA or cosmid DNA expression vectors encoding a chimeric protein of the invention. A primary advantage of the optically active polypeptides of the invention is that they are prepared by normal protein biosynthesis, thus avoiding organic synthesis and the requirement for customized unnatural amino acid analogs. The constructs can be expressed in *E. coli* in large scale for in vitro assays. Purification from bacteria is simplified when the sequences include tags for one-step purification by nickel-chelate chromatography. The construct can also contain a tag to simplify isolation of the fluorescent indicator. For example, a polyhistidine tag of, e.g., six histidine residues, can be incorporated at the amino terminal end of the fluorescent protein. The polyhistidine tag allows convenient isolation of the protein in a single step by nickel-chelate chromatography. Alternatively, the substrates can be expressed directly in a desired host cell for assays in situ.

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies or antigen.

It should be understood that a nucleic acid sequence can also f unction as the responsive element in another embodiment of the invention. For example, a response may result from a DNA binding protein interaction with the chimeric polypeptide of the invention when the chimeric polypeptide includes a DNA sequence having a DNA binding protein motif.

Screening Assays

The invention features a method for determining the presence of an activity in a sample, by contacting the sample with a chimeric protein of the invention; exciting the chimeric protein; and measuring the amount of an optical property of the chimeric protein in the presence and absence of activity, such that a change in the optical property is indicative of activity in the sample. A series of standards, with known levels of activity, can be used for to generate a standard curve. The optical event, such as intensity of fluorescence, that occurs following exposure of the sample to the chimeric protein is measured, and the amount of the optical property is then compared to the standard curve. A series of cellular standard, with known levels of activity, can be used to generate a standard curve, or to provide reference standards. The optical event, such as fluorescence, that occurs following exposure of the cell sample to the chimeric protein is measured, and the amount of the optical property (e.g., fluorescence) is then compared to the standards in order to generate a relative measure of activity.

In another embodiment, the invention features a method for determining if a cell exhibits an activity, which includes transfecting the cell with a nucleic acid encoding a chimeric protein of the invention; exciting the chimeric protein; and measuring the amount of an optical property in the presence of the activity and in the absence of the activity, such that a change in the optical property is indicative of activity.

Typically, the optical property is calibrated against standard measurements to yield an absolute amount of protein activity.

It is understood that the cell containing a nucleic acid sequence encoding a chimeric protein of the invention can be used to co-transfect other genes of interest in order to determine the effect of the gene product of that gene on the cell or the responsive polypeptide of the chimeric protein. Therefore, a cell containing such a nucleic acid sequence is a composition provided by the present invention. For example, a neural cell which expresses the chimeric protein exemplified in the Examples (FlaSh), can be used to co-transfect other genes of interest, such as serotonin, in order to determine the effect of serotonin on the cell as measured by activity of the Shaker ion channel. Other equivalent examples will be apparent or easily constructed by those of skill in the art without much need for further experimentation.

The invention can be used in screening assays to determine whether a compound (e.g., a drug) alters the activity of a particular protein (e.g., ligand binding to a receptor). In one embodiment, the assay is performed on a sample containing the chimeric protein in vitro. A sample containing a known amount of activity, such as an enzymatic activity, is mixed with a chimeric protein substrate of the invention, with the co-factors required for activity, and with a test compound. The amount of the enzyme activity in the sample is then determined by measuring the amount of an optical property, such as a fluorescent property, at least a first and second time after contact between the sample, the chimeric protein substrate of the invention, and any co-factors or components required to conduct the reaction, and the test compound. Then the amount of activity per mole of enzyme, for example, in the presence of the test compound is compared with the activity per mole of enzyme in the absence of the test compound. A difference indicates that the test compound alters the activity of the enzyme. In general a change in the optical parameter by any measurable amount between activity in the presence of the test compound as compared with the activity in the absence of the test compound, is indicative of activity.

In another embodiment, the ability of a compound to alter the activity of a particular protein in vivo is determined. In an in vivo assay, cells transfected with a expression vector encoding a substrate of the invention are exposed to different amounts of the test compound, and the effect on the optical parameter, such as fluorescence, in each cell can be determined. Typically, the difference is calibrated against standard measurements to yield an absolute amount of protein activity. This provides a method for screening for compounds which affect cellular events (e.g., receptor-ligand binding, protein-protein interactions or protein kinase activation). In a given cell type, any measurable change between activity in the presence of the test compound as compared with the activity in the absence of the test compound, is indicative of activity. In the present examples, a 0.1% change representing $\frac{1}{50}$ of the signal was measurable, for example.

The materials of the invention are ideally suited for a kit for determining the presence of an activity in a sample. Such a kit may contain a container containing a chimeric protein comprising an optically active polypeptide linked to a responsive polypeptide, or fragment thereof, which undergoes a change in response to the activity, wherein optical properties of the sensor are altered in response to the change in the responsive polypeptide, or fragment thereof. In another embodiment, a kit of the invention contains an isolated nucleic acid sequence which encodes a chimeric protein comprising amino acid sequences encoding an optically active polypeptide linked to a responsive polypeptide, or responsive fragment thereof, which undergoes a conformational change in response to a cell signaling event, wherein an optical property of the sensor is altered in response to the conformational change in the responsive polypeptide, or responsive fragment thereof. The nucleic acid sequence of the later kit may be contained in a host cell, preferably stably transfected. The cell could optionally be transiently transfected. Thus, the cell acts as an indicator kit in itself.

Transgenic Animals

In another embodiment, the present invention relates to transgenic animals that have cells that express an optically active polypeptide operatively fused to a responsive polypeptide, or fragment thereof, which normally has two or more conformational shapes, and which undergoes a conformational change during a cell signaling event. Transgenic animals expressing high levels of the tagged transgene may be obtained, for example, by over-expression of the transgene with an enhanced promoter and/or with high copy numbers of the transgene. The transgenic animal may be heterozygous or homozygous for an ablated or disrupted endogenous sensor gene. In specific embodiments, the invention features a transgenic mammal having a fluorescent-tagged channel protein, such as a GFP-potassium channel.

The "non-human animals" of the invention comprise any non-human animal having nucleic acid sequence which encodes a chimeric protein of the invention. Such non-human animals include vertebrates such as rodents, non-human primates, sheep, dog, cow, pig, amphibians, reptiles and fish. Preferred non-human animals are selected from the rodent family including rat and mouse, most preferably mouse. The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al., *Proc. Natl. Acad. Sci. USA* 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

Viral infection can also be used to introduce transgene into a non-human animal (e.g., retroviral, adenoviral or any other RNA or DNA viral vectors). The developing nonhuman embryo can be cultured in vitro to the blastocyst stage. During this time, the blastomeres can be targets for retro viral infection (Jaenich, R., *Proc. Natl. Acad. Sci USA* 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retrovirus carrying the transgene (Jahner, et al., *Proc. Natl. Acad. Sci. USA* 82:6927–6931, 1985; Van der Putten, et al., *Proc. Natl. Acad. Sci USA* 82:6148–6152, 1985). Transfection is easily and efficiently obtained by culturing the blastomeres on a monolayer of virus-producing cells (Van der Putten, supra; Stewart, et al., *EMBO J.* 6:383–388, 1987). Alternatively, infection can be performed at a later stage. Virus or virus-producing cells can be injected into the blastocoele (D. Jahner et al., *Nature* 298:623–628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retro viral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. *Nature* 292:154–156, 1981; M. O. Bradley et al., *Nature* 309: 255–258, 1984; Gossler, et al., *Proc. Natl. Acad. Sci USA* 83: 9065–9069, 1986; and Robertson et al., *Nature* 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., *Science* 240: 1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extra-chromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode the chimeric proteins of the invention which may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

EXAMPLES

Example 1
Chimeric Constructs of the Shaker Potassium Channel and GFP

Figure 1A:
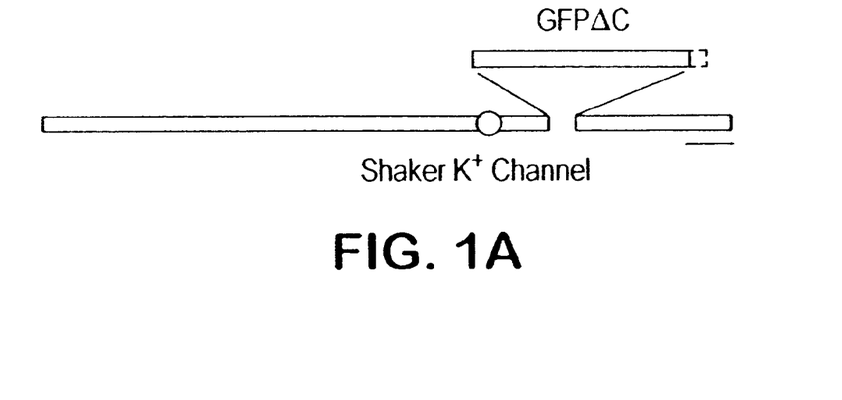
FIG. 1A is a diagram of the FlaSh construct, consisting of a green fluorescent protein gene inserted in-frame into the Shaker K+ channel.

ShH4 (GenBank X78908; Kamb et al., *Neuron* 1(5):421, 1988) had been cloned in pBluescript (Stratagene), and site directed mutagenesis was used to engineer the point mutaion was engineered into the pore region of the channel, called W434F. W434F prevents ion conduction, but preserves the channel's gating rearrangements in response to voltage changes (Perozo et al., 1993). The core of the Shaker channel, including the N-terminal assembly domain and the transmembrane segments, is highly conserved (Stuhmer et al., 1989; Drewe et al., 1992; Li et al., 1992; Shen et al., 1993), and likely to be intolerant to large insertions. Therefore, GFP was fused in-frame at a site just after the sixth transmembrane segment (S6, see FIG. 1A).

As the crystal structure of GFP indicates that its C-terminus is disordered from amino acid 330–238 (Ormo et al, 1996; Yang et al., 1996), and several amino acids can be removed without disrupting GP fluorescence (Dopf and Horigan, 1996), amino acids 233–238 were deleted in the construct. Thus GFPΔC was amplified from the plasmid TU#65 (Chalfie, M., et al. (1994) Science, 263:802–805) using the primer sequence 5'-CCACTAGTAAA GGAGAAGAACTTTTC-3' (SEQ ID NO:1) and 5'-GGACT AGTGCCATGTGTAATCCCAGCAGCTGT-3' (SEQ ID NO:2). These primers amplify amino acids 2–233 of GFP and add SpeI restriction sites in-frame to both ends.

Figure 1B:
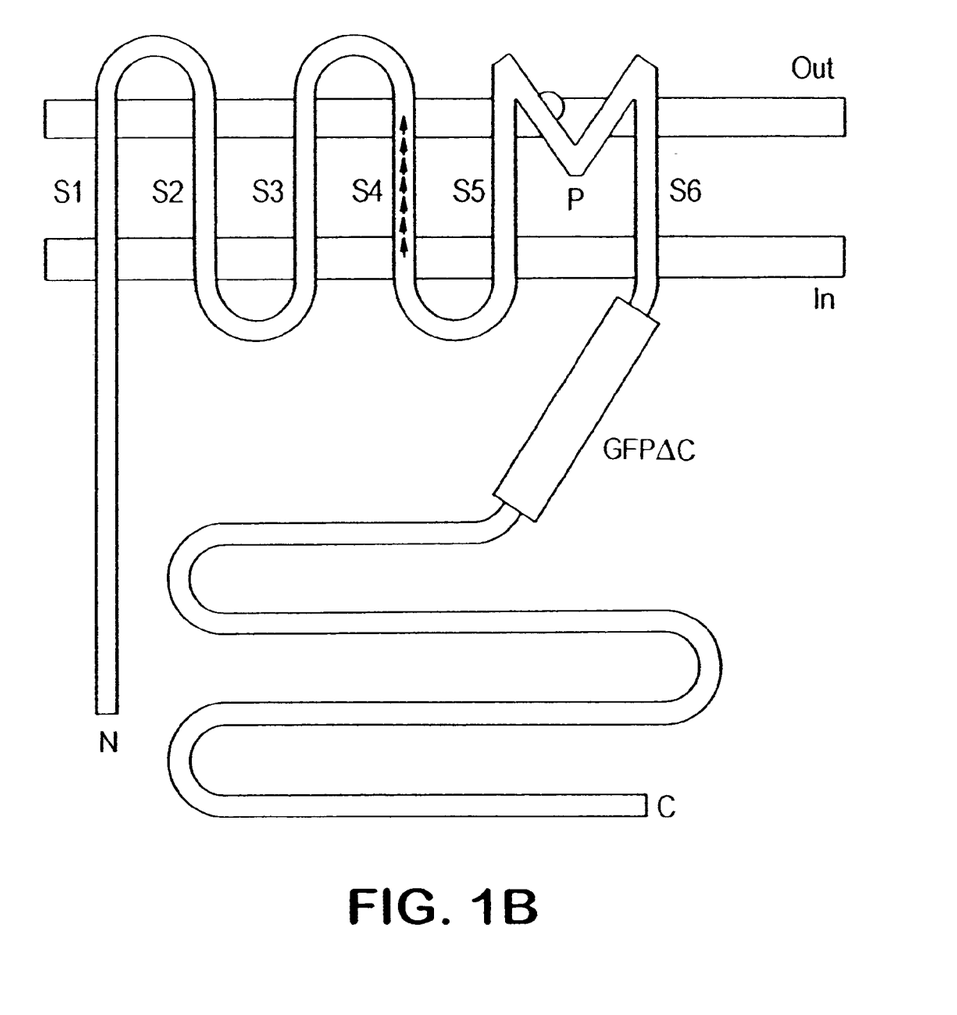
FIG. 1B is a schematic drawing showing the putative orientation of the FlaSH protein in the cell membrane. In=inside the cell membrane; Out=outside the cell membrane.

GFPΔC was inserted into ShH434F at the SpeI restriciton site using standard techniques and the orientation of the insert was verified by digesting with NcoI, which cuts asymmetrically in GFPΔC and ShH4. A Hpa I digest was used to verify that only a single copy of GFPWΔC was inserted into ShH4W434F. Thus, the structured, fluorescent core of GFP was directly linked to the movable parts of the channel (see FIG. 1A). This construct was called Shaker-W434GFPΔC@S6, or "FlaSh." The predicted membrane orientation of FlaSh is shown in FIG. 1B.

Example 2
In vivo Parameters and Fluorescence of FlaSh

FlaSh cDNA was transcribed using Megascript T7 (Ambion, Austin, Tex.) with a 4:1 methyl CAP to rGTP ratio, and the precipatied cRNA was resuspended in Ultrapure water (Specialty Media, Labellete, N.J.) for injection. Xenopus oocytes were injected, using standard methods (Isacoff, E. Y., et al. (1990) Nature, 345:530–534) with cRNA transcribed from FlaSh.

Two-electrode voltage clamping was performed with a Dagan CA-1 amplifier (Dagan Corporation, Minneapolis, Minn.). External solution was NaMES (110 mM NaMES, 2 mM Ca(MES)2, 10 mM Hepes, pH 7.5). Capacitance compensation was performed from a holding potential of +60 mV. An HC120-05 photomultiplier (Hamamatsu, Bridgewater, N.J.) was used for fluorescence measurements, on a Nikon TMD inverted microscope. Data was sampled at 4 kHz and fluorescence signals were low-pass filtered at 1 kHz with an 8-pole bessel filter (Frequency Devices, Haverhill, Mass.). Data was acquired onto a Digidata 1200 A/D interface (Axon Instruments, Foster City, Calif.). Data Acquisition and analysis were done with Axon Instruments Pclamp 6. Illumination was with a 100 W Hg Arc lamp. Exciting and emitted light were filtered through an HQ-GFP filter (Chroma Technology, Brattleboro, Vt.), with the following bandpass: ex: 425–475 nm, di: 480 nm long-pass, em: 485–535 nm.

Figure 4A:
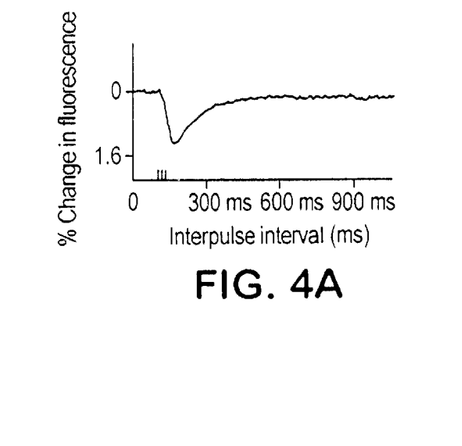
FIGS. 4A–H are a series of traces demonstrat[es]ing that FlaSh response to brief pulses can be detected in single sweeps. Fluorescence-voltage relations were constructed from the amplitudes of the "on" fluorescence change from steps long enough to reach steady-state (with length of steps indicated by vertical lines on X axis).
Figure 4B:
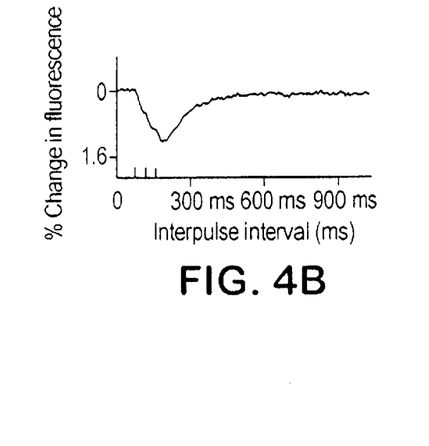
Figure 4C:
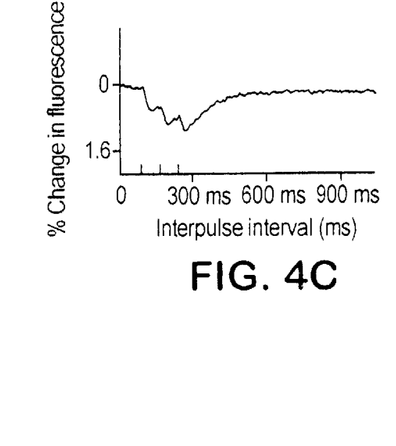
Figure 4D:
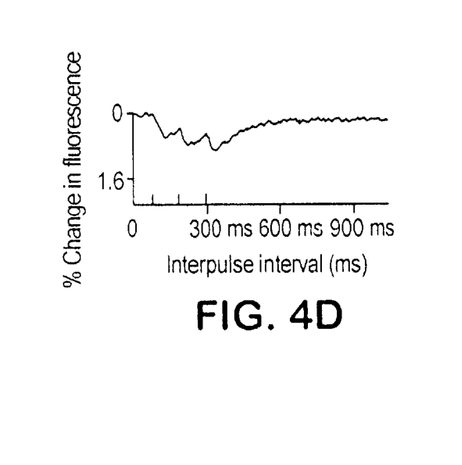
Figure 4E:
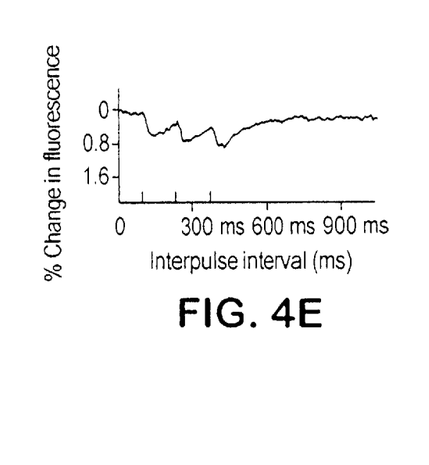
Figure 4F:
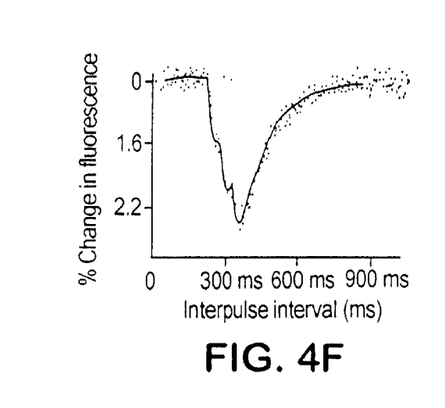
Figure 4G:
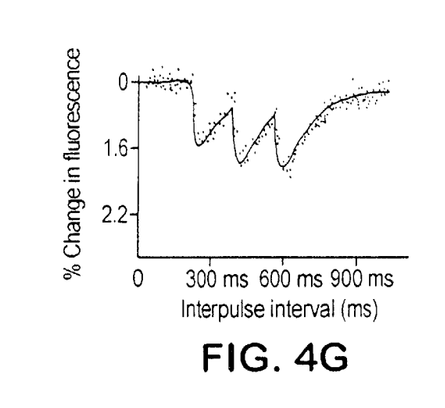
Figure 4H:
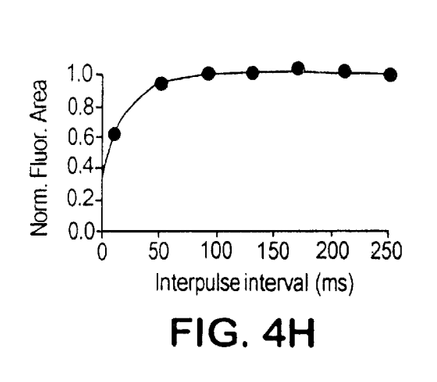

Charge-voltage relations were constructed from the integrated "off" gating currents, evoked by repolarizations to −80 mV, after depolarizations that were long enough for the "on" gating current to decay to completion. Fluorescence-voltage relations were constructed from the amplitudes of the "on" fluorescence change from steps long enough to reach steady-state. Fluorescence traces in FIGS. 4A–E were digitally RC filtered at 300 Hz. Linear reconstructions in FIGS. 4F&G were performed with Matlab software (MathWorks).

Confocal images were acquired on a Nikon PCM-2000 microscope using the 488 nm line of an Argon laser. Images were analyzed using the public domain NIH Image program (developed at the U.S. National Institutes of Health). Oocytes injected with W434GFPΔC@56 showed green membrane fluorescence, indicating that GFP was appropriately targeted.

Figure 2A:
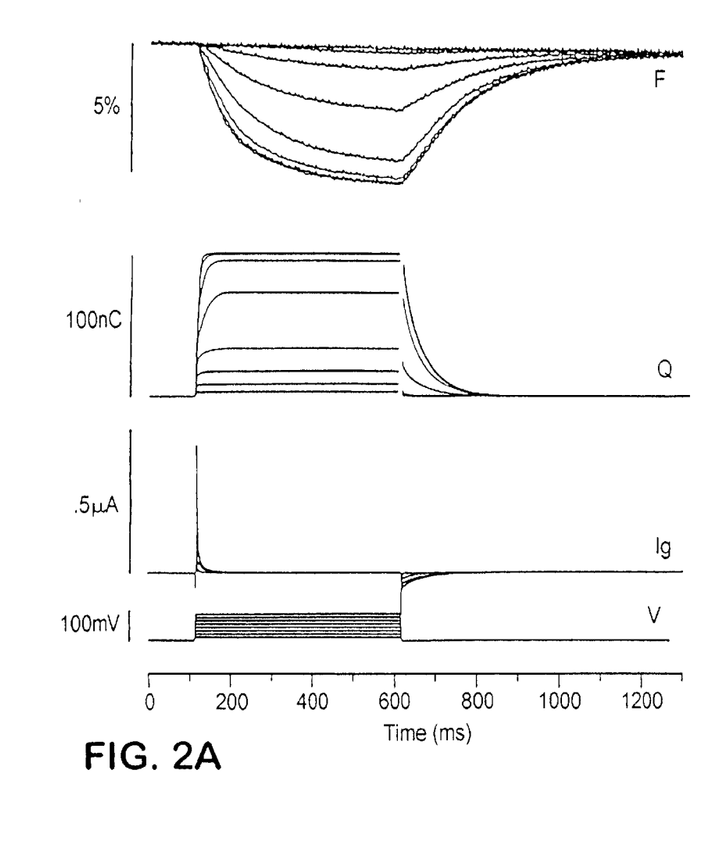
FIG. 2A is a series of traces showing the simultaneous two-electrode voltage clamp recording and photometry indicating fluorescence changes in response to voltage steps (v) between −60 mV and +10 mV, in 10 mV increments. F=fluorescence change with the bar at the y axis=5% change; Q=total gating charge with the bar at the y axis=100 nC; Ig=gating current with the bar at the y axis=0.5 $\mu$A; V=voltage with the bar at the y axis=100 mV.
Figure 2B:
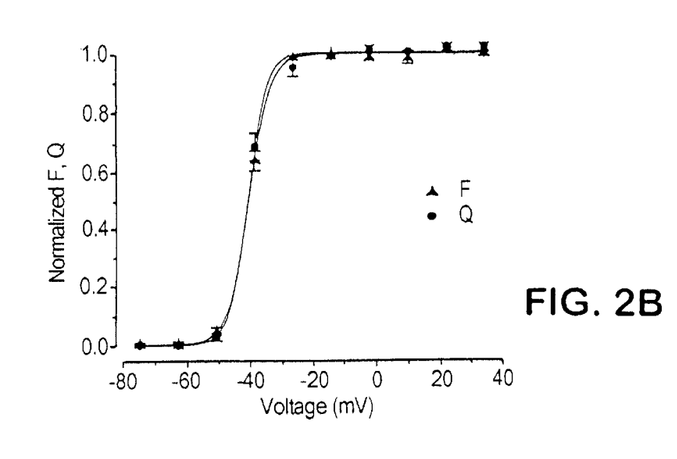
FIG. 2B is a graph showing the correlation of FlaSh fluorescence with Shaker action gating.

As expected the W434F mutation abolished ionic current through the sensor. Voltage steps from a holding potential of −80 mV evoked only "on" and "off" gating currents (FIG. 2A). A maximum fluorescence decrease of 5.1±0.7% (n=7) was observed in response to steps that moved all of the gating change. Small depolarizing voltage steps, which evoked only the gating charge component that was minor and fast, produced no fluorescence change. The relation of the steady-state gating charge to voltage was sigmoidal, and correlated closely with he steady-state gating charge to voltage relation (FIG. 2B). Thus, in FlaSh, the fluorescence emission of GFP is coupled to the voltage dependent rearrangements of the Shaker channel.

The FlaSh protein was very stable, as judged by gating a current and fluorescence measurements. Moreover, expression did not decline over a period of two weeks in Xenopus oocytes. No bleaching was visible after over five minutes of measurement with nearly continuous broad-band (425–475) excitation. In addition, FlaSh continued to respond to voltage when the temperature was increased from 22° C. to 37° C. The rates of both the onset and recovery of the fluorescence change were increased by 2.0±0.3 (n=3) fold at the higher temperature.

Although the fluorescence of FlaSh follows the voltage dependence of Shaker activation, the kinetics of the "on" and "off" fluorescence changes ($F_{on}$ and $F_{off}$) were slower than the movement of the gating charge ($Q_{on}$ and $Q_{off}$) (see FIG. 4). At steps to 0 mV, $Q_{on}$ was approximately 30-fold faster (p<0.0001) than $F_{on}$ ($\tau_{(Qon)}$=2.8±0.4 ms, $\tau_{(Fon)}$=85±10 ms, n=5). The kinetics of the fluorescence change indicate that rearrangement in the voltage sensor of Shaker may trigger (but not cause directly) the change in GFP fluorescence.

The fluorescence response of FlaSh cannot be a direct consequence of N-type inactivation because $F_{on}$ and $F_{off}$ were slower than the onset and recovery of N-type inactivation. As shown earlier (Bezanilla et al., 1991), the onset of gating charge immobilization, and thus N-type inactivation, closely followed $Q_{on}$ (FIG. 3, $I_g$), which was more than an order of magnitude faster than $F_{on}$. Moreover, the immobilized $Q_{off}$ at −80 mV, following large depolarizations, returned approximately twice as fast (p<0.001) as $F_{off}$ ($\tau_{(Qoff)}$=72±7 ms, $\tau_{(Foff)}$=160±12 ms, n=7).

Figure 2C:
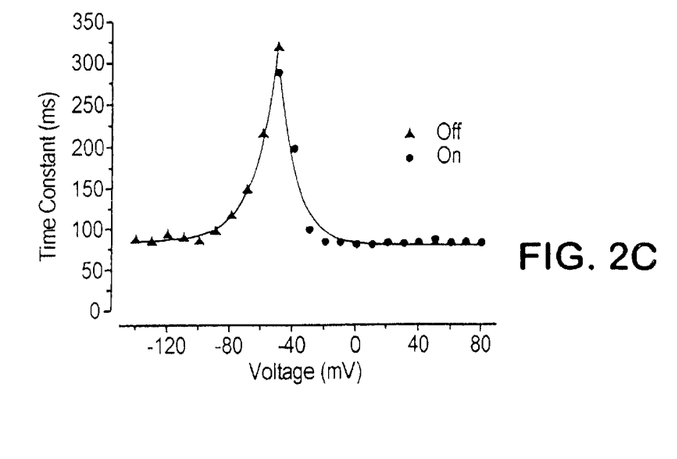
FIG. 2C is a graph illustrating the independence of the kinetics of fluorescence change of FlaSh from voltage at extreme potentials.

The delay in the fluorescence change may arise from a time-dependent event in GFP, or a show rearrangement in Shaker. The fluorescence change lacks intrinsic voltage sensitivity, whatever its mechanism, since the time-constants of both $F_{on}$ and $F_{off}$ saturate at voltages outside of the voltage range of activation (FIG. 2C).

Figure 3:
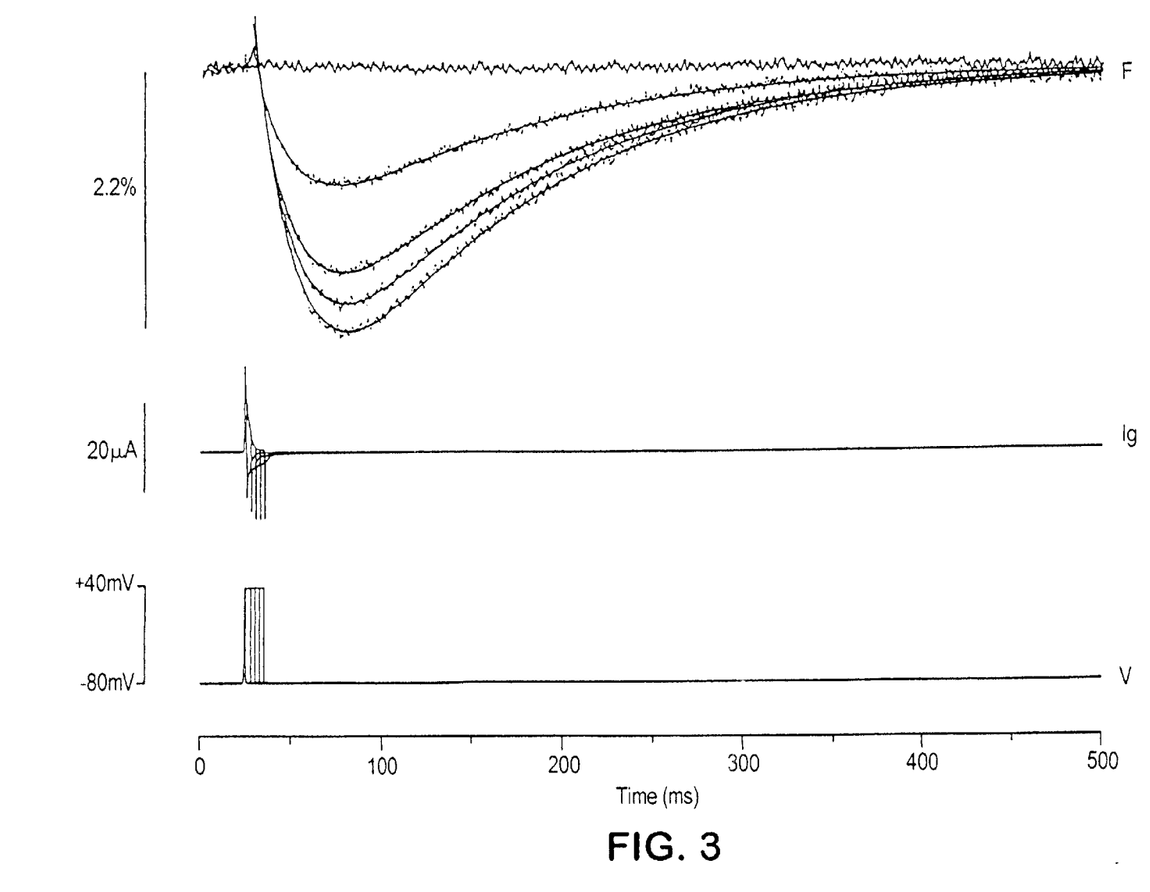
FIG. 3 is a series of traces showing that brief depolarizations of cells expressing FlaSh evoke stereotypical fluorescence responses. F=fluorescence change with the bar at the y axis=2.2% change; Ig=gating current with the bar at the y axis=20 $\mu$A; V=voltage with the bar at the y axis=120 mV.

To determine whether FlaSh could respond to short-lasting electrical activity, we explored its fluorescence kinetics in response to brief voltage pulses. These voltage transients moved a fraction of the total gating charge, and steps of 3 ms and longer evoked long, stereotypical fluorescent responses (FIG. 3). While the magnitude of the fluorescence change was related to the duration of the step, its kinetics of onset and recovery were constant. The entire collection of fluorescent responses was well-fit by a double-exponential with time constants of 23 ms for $F_{on}$ and 105 ms for $F_{off}$. These kinetics are, respectively, 4-fold, and 1.5-fold faster than those of the fluorescence changes evoked by long steps.

This stereotyped fluorescence response was clearly visible in single-sweep recordings (FIG. 4). Subsequent events that occurred during the time-course of the fluorescence change summated with the original response. The unitary responses were visible in the summated response when the trains of electrical events were at frequencies of 20 Hz or less. Trains at 100 Hz produced a fused response in which the individual events could not be distinguished by eye.

For a short train of identical brief pulses, the integral of the fluorescence response was constant at frequencies of 20 Hz and lower, but declined at higher frequency. The decline occurred as the peak response approached the maximal fluorescence change, that is, as the sensor population became saturated. In the low frequency range, a linear filter model, with the kinetics of the unitary response based on the stereotypical shape of the FlaSh fluorescence change (FIG. 3) accounted well for the shape of the fluorescence response to a pulse. Given the acceleration of FlaSh kinetics when temperature is increased from 22° C. to 37° C., the maximal firing rate over which FlaSh will be linear may be twice the frequency cutoff of the cooler temperature.

Example 3
Transgenic Mice Expressing Optical Sensors

Transgenic mice that can produce a chimeric protein encoding an optically active polypeptide linked to a responsive peptide are produced according to methods well known in the art. For example, young female mice are injected with hormones to induce superovulation, and are mated. The one-celled embryos are collected, and the pronuclei injected with a purified DNA solution containing the constructs which encode FlaSh. The injected eggs are cultured briefly, and re-implanted into pseudopregnant female mice. Genomic DNA is prepared from each progeny, and analyzed by PCR or Southern blot to determine the mouse's genotype. Mice who carry the transgene are subsequently mated in order to produce a line of mice.

Using these method mice are produced which contain transgenes encoding the optically active polypeptides responsive to cell signaling of the invention. In order to target the construct to specific cell types, transgenic mice are produced which carry the optically active polypeptides responsive to cell signaling genes encoding the under the control of specific promoters. Examples of such constructs are genes encoding FlaSh under the control of the neurofilament promoter, which specifically targets the expression of FlaSh to the neurons.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. All patents and publications cited herein are hereby incorporated by reference.

What is claimed is:

1. A chimeric protein sensor comprising green fluorescent protein (GFP) and a Shaker potassium channel (W434F), wherein the Shaker potassium channel undergoes a change in response to a cell signaling event and wherein fluorescence emission of the sensor is correspondingly altered in response to the change in the Shaker potassium channel.

2. The chimeric protein sensor of claim 1, wherein the GFP has up to eight amino acids deleted from the C-terminus.

3. A kit for determining the presence of an activity in a sample, comprising:

a chimeric protein sensor comprising GFP and a Shaker potassium channel (W434F), wherein the Shaker potassium channel undergoes a change in response to a cell signaling event and wherein fluorescence emission of the sensor is correspondingly altered in response to the change in the Shaker potassium channel.

4. A chimeric protein sensor comprising GFP inserted into the pore region of a Shaker potassium channel (W434F) and wherein fluorescence emission of the sensor is correspondingly altered in response to rearrangement of the Shaker potassium channel in the sensor.

5. The chimeric protein of claim 4 wherein the GFP has up to eight amino acids deleted from the C-terminus.

* * * * *